United States Patent [19]

Sumner, Jr.

[11] Patent Number: 4,935,540

[45] Date of Patent: Jun. 19, 1990

[54] PROCESS FOR THE PREPARATION OF ARYLOXYACETIC ACID

[76] Inventor: Charles E. Sumner, Jr., 4613 Woodclift Dr., Kingsport, Tenn. 37664

[21] Appl. No.: 283,098

[22] Filed: Dec. 12, 1988

[51] Int. Cl.$^5$ ............................................. C07C 51/16
[52] U.S. Cl. ..................................... 562/421; 562/471
[58] Field of Search ................................ 562/421, 471

[56] References Cited

U.S. PATENT DOCUMENTS 4,238,625 12/1980 Fiege et al. ......................... 562/421
4,247,716 1/1981 Kiyoura .............................. 562/421

*Primary Examiner*—Paul J. Killos
*Attorney, Agent, or Firm*—Charles R. Martin; William P. Heath, Jr.

[57] ABSTRACT

Process for the preparation of an aryloxyacetic acid by oxidation of aryloxyethanol of the formula:

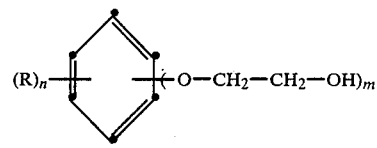

wherein
m represents 1 or 2,
n represents the numeral which results from the difference between 6 and m and R either individually or independently of one another represents hydrogen, alkyl, cycloalkyl, aryl, aralkyl, alkoxy, cycloalkoxy, aryloxy, halogen, alkylcarbonyl, arylcarbonyl, carboxyl or nitro, or represents a benzene ring fused to the phenyl ring, in an aqueous alkaline reaction medium at a temperature in the range of 0° C. to the boiling point of the reaction medium in the presence of a catalytic amount of a catalyst comprised of palladium, thallium and carbon to form the corresponding alkali metal ester and contacting the alkali metal ester with a mineral acid.

7 Claims, No Drawings

PROCESS FOR THE PREPARATION OF ARYLOXYACETIC ACID

This invention relates to a process for the preparation of aryloxyacetic acids by oxidation of aryloxyethanols.

The oxidation of aryloxyethanols to corresponding acids is well known in the art. For example, U.S. Pat. No. 4,238,625 discloses such an oxidation using a catalyst comprised of palladium and other metals. Oxidation using a palladium and silver catalyst is disclosed in U.S. Pat. No. 4,247,716.

We have now discovered that yields of acid can be significantly enhanced if a combination of palladium and thallium is used instead of palladium alone or in conjunction with other metals disclosed in the prior art.

The process of our invention is composed of three steps. In the first step the aryloxyethanol is oxidized to the corresponding alkali metal aryloxyacetate using a palladium and thallium catalyst. The next step is to separate the alkali metal aryloxyacetate from the catalyst. The aryloxyacetic acid is then prepared by contacting the aryloxyacetate with a mineral acid.

The process of this invention can be illustrated by references to a preferred embodiment. In this embodiment resorcinol bis(B hydroxyethyl)ether having the structure:

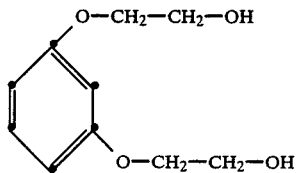

is contacted with oxygen in a sodium containing aqueous alkaline reaction medium having a pH of greater than 10 at a temperature in the range of 80° to 90° C. in the presence of 5 to 10 weight percent, based on the weight of the aryloxyethanol, of a catalyst comprised of palladium and thallium on carbon wherein the mole ratio of thallium to palladium is about 0.1:1:0.1. The oxidation product is the sodium ester of 1,3-phenylenedioxydiacetic acid corresponding to the structure:

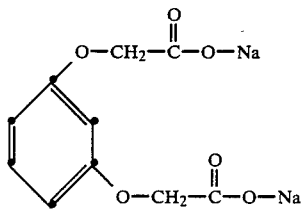

Next, the ester is separated by filtration from the catalyst. Then the ester is contacted with a mineral acid to prepare the corresponding acid corresponding to the structure:

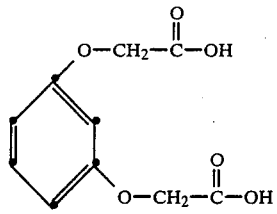

The aryloxyacetic acids prepared by the process of this invention correspond to the structure:

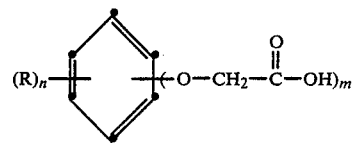

wherein
m represents 1 or 2,
n represents the numeral which results from the difference between 6 and m and R either individually or independently of one another represents hydrogen, alkyl, cycloalkyl, aryl, aralkyl, alkoxy, cycloalkoxy, aryloxy, halogen, alkylcarbonyl, arylcarbonyl, carboxyl or nitro, or represents a benzene ring fused to the phenyl ring.

Alkyl radicals can be straight chain or branched hydrocarbon radicals with 1 to 12, preferably 1 to 6, carbon atoms. Preferred alkyl radicals for the process according to the invention are lower alkyl radicals. Examples of alkyl radicals which may be mentioned are methyl, ethyl, propyl, isopropyl, butyl, isobutyl, sec.-butyl, tert.-butyl, pentyl, isopentyl, tert. amyl, hexyl, isohexyl, heptyl, isoheptyl, tert.-octyl, isooctyl, nonyl, isononyl, decyl, isodecyl, undecyl, isoundecyl, dodecyl and isododecyl.

Cycloalkyl radicals can be cyclic hydrocarbon radicals with 4 to 9, preferably 5 and 6, carbon atoms. The cyclopentyl and the cyclohexyl radical may be mentioned as examples.

The phenyl and the naphthyl radical may be mentioned as preferred aryl radicals for the process according to the invention.

Aralkyl radicals can be alkyl radicals with 1 to 6 carbon atoms, preferably lower alkyl radicals, which are substituted by an aromatic hydrocarbon radical with 6 to 12 carbon atoms, preferably phenyl and naphthyl. Benzyl, α,α-dimethyl-benzyl groups may be mentioned by way of example.

Alkoxy radicals can consist of up to 12, preferably of up to 6, carbon atoms in the aliphatic part. A lower alkoxy radical is particularly preferred. The following may be mentioned as examples of alkoxy radical: methoxy, ethoxy, propoxy, isopropoxy, butoxy, isobutoxy, tert butoxy, pentoxy, isopentoxy, hexoxy, isohexoxy and methylenedioxy.

The cyclopentoxy and the cyclohexoxy radical may be mentioned as preferred cycloalkoxy radicals.

The phenoxy and the naphthoxy radical may be mentioned as preferred aryloxy radicals.

Halogens can be fluorine, chlorine, bromine and iodine, preferably chlorine and bromine.

Lower alkylcarbonyl radicals ($C_1$ to $C_6$), such as the acetyl radical, may be mentioned as preferred alkylcarbonyl radicals.

The benzoyl radical may be mentioned as a preferred arylcarbonyl radical.

Fusion of a benzene ring to the phenyl ring can, for example, produce the naphthalene ring system.

Fusion of a cycloalkane ring to the phenyl ring can, for example, produce the tetralin ring system.

It is of course possible for the abovementioned substituents to be substituted by usual radicals which are inert under the reaction conditions. Fluorine, chlorine, methyl and methoxy may be mentioned as examples.

One preferred embodiment is where n is 4, R is hydrogen and m is 2. A particular preferred embodiment is the meta and para isomer, with the meta being most preferred. Another preferred embodiment is where R represents a benzene ring fused to the phenyl ring to the naphthalene structure and m is 2. A particularly preferred embodiment is the 2,7-isomer.

The aryloxyethanols which are used to prepare the aryloxyacetic acids are prepared by methods well known in the art. For example, the aryloxyethanols can be prepared by addition reaction of ethylene oxide with the hydroxyl group or groups of an appropriately substituted phenol or naphthol (Monatshefte Chemie 77, (1947) 80 to 85).

Representative examples of aryloxyethanols are phenoxyethanol, 2-methyl phenoxyethanol, 3-methyl-phenoxyethanol, 4-methyl-phenoxyethanol, 2,3-dimethyl-phenoxyethanol, 2,4-dimethyl-phenoxyethanol, 2,5-dimethyl-phenoxyethanol, 2,6-dimethyl-phenoxyethanol, 3,4-dimethyl-phenoxyethanol, 3,5-dimethyl-phenoxyethanol, 2-chloro-phenoxyethanol, 3-chloro-phenoxyethanol, 4-chloro-phenoxyethanol, 2-chloro-4-methyl-phenoxyethanol, 2-chloro-5-methyl-phenoxyethanol, 2-chloro 6-methyl-phenoxyethanol, 4-chloro-2-methyl-phenoxyethanol, chloro-3-methyl-phenoxyethanol, 2-chloro4-fluoro-phenoxyethanol, 2,3-dichloro-phenoxyethanol, 2,4-dichloro-phenoxyethanol, 2,5-dichloro-phenoxyethanol, 2,6-dichloro-phenoxyethanol, 3,4-dichloro-phenoxyethanol, 3,5-dichloro-phenoxyethanol, 4,6-dichloro-2-methyl-phenoxyethanol, 2,6-dichloro-4-methyl-phenoxyethanol, 2,6-dichloro-3-methyl-phenoxyethanol, 2,4-dimethyl-6-chloro-phenoxyethanol, 2,6-dimethyl-4-chloro-phenoxyethanol, 2,4,5-trichloro-phenoxyethanol, 2,4,6-trichloro-phenoxyethanol, 3,4,5-trichloro-phenoxyethanol, 2,3,4-trichloro phenoxyethanol, 4-nonylphenoxyethanol, α-naphthoxyethanol and β-naphthoxyethanol. Preferred aryloxyethanols for the process according to the invention are phenoxyethanol, 4-chloro-2-methyl-phenoxyethanol, 2,4-dichloro-phenoxyethanol and 2,4,5 trichloro-phenoxyethanol.

The first step of the process of this invention is conducted by bringing oxygen or an oxygen-containing gas, such as air, into good contact with the aryloxyethanol in an aqueous medium, which also contains the source of the alkali metal cation and the catalyst. The reaction medium can be a solution or a suspension; however, a solution is preferred.

In general, the reaction is carried out at atmospheric pressure, but oxidation can also be carried out at higher or lower pressures. In general, the-process according to the invention is carried out in the pressure range of 0.5–10 bar.

The aryloxyacetate compound which results from the first step of the invention corresponds to the structure:

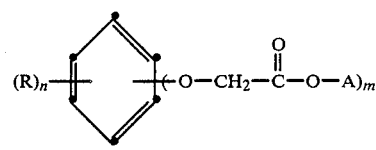

wherein n, m and R are as described above and A is an alkali metal cation.

It is important that the catalyst be separated from the aryloxyacetate. This can be accomplished by method well known in the art, such as centrifugation or filtration. Due to cost, filtration is perferred.

The aryloxyacetate which is separated from the catalyst is then converted into the corresponding aryloxyacetic acid by contact with a mineral acid according to techniques well known in the art, such as disclosed in U.S. Pat. No. 4,238,625.

The palladium useful in the catalyst of this invention can be in a variety of forms. Elemental palladium metal can be used. Other palladium compounds, such as the oxides can be used.

The thallium useful as the catalyst in this invention can exist in many different forms and oxidation states. Examples of thallium compounds which can be used are thallium (I) nitrate, thallium (III), thallium (I) oxide, thallium (III) oxide, thallium (I) acetate and thallium (I) hydroxide.

The use of thallium in this invention is particularly important as regards catalyst life. If only palladium is used, the palladium quickly deactivates, is not reusable, and results in formation of significant amounts of by-products such as phenolic compounds.

The carbon useful for the catalyst support can comprise a low sulfur, pophilic, pulverulent type, which is high in silicon and has an ordered structure. Materials of this nature are well known in the art.

The relative amounts of metals in the catalyst can vary widely. Broadly, the mole ratio of thallium to pallidium can be 0.01 to 2.0 moles of thallium per mole of palladium.-preferably the ratio is 0.05 to 0.8 mole of thallium per mole of palladium with 0.1 to 0.5 mole of thallium per mole of palladium being most preferred.

The catalyst useful in this invention is prepared by applying the metals to a carbon support according to methods well known in the art. According to one method, 13.0 grams of commercially available 5% palladium on carbon was slurried in 200 mL of water in a 500 mL 3-neck flask equipped with a mechanical stirrer, reflux condenser, an argon inlet, a hydrogen inlet, and a heating mantle. The mixture was heated to reflux while being vigorously stirred and purged with argon. Hydrogen was bubbled through the mixture at such a rate that the mixture was saturated with hydrogen. The mixture was contacted with hydrogen for twenty minutes, then was purged with argon while still being refluxed for minutes. A solution of thallium(I) nitrate was added and the resulting mixture was refluxed for an additional 15 minutes. The resulting catalyst was collected by filtration.

The amount of catalyst can vary within wide limits depending on the desired rate of oxidation. In general, the amount of catalyst is 5 to 20 weight percent, preferably 5 to 10 weight percent, based on the weight of aryloxyethanol. Of course, virgin carbon can be added to increase the number of recycles of a catalyst charge.

Preferably the steps of the process are performed in the sequence described; however, the sequence of the steps can be modified if desired. For example, the catalyst can be added to the mixture or solution containing aqueous alkali metal and aryloxyethanol. One can also add the mixture of aqueous alkali and aryloxyethanol to the catalyst. Finally, one can also first take the catalyst, a part of the aqueous alkali metal solution and then add the aryloxyethanol together with the remaining alkali metal solution.

The oxidation step of the process of the invention is carried out in an aqueous alkalin reaction medium. Sodium hydroxide or potassium hydroxide are preferred compounds to prepare the alkali reaction medium. The amount of alkali metal cation is chosen so as to provide 1 to 6 mols of alkali metal cation per mol of carboxyl group formed.

The concentration of the aryloxyethanol in the aqueous alkaline reaction mixture is in general selected so that the resulting aryloxyacetic acid is present in solution during the reaction. Concentrations of 2% to 25% by weight are advantages. If desired, the solubility can be improved by the addition of inert solvents or solubilizing agents.

The temperature for the oxidation step can lie between 0° C. and the boiling point of the reaction mixture. The specific reaction temperature depends on such factors as the alkali concentration, the properties of the educts and the properties of the products. Suitable temperature ranges typically are from 50° to 150° C., preferably from 80° to 110° C. The first step in the oxidation of aryldioxydiethanols, i.e., formation of the half-acid intermediate, is less dependent upon temperature than is the second step of the oxidation, which is the conversion of the half-acid to the aryldioxydiacetic acid.

The aryloxyacetic acids prepared by this invention are useful for the preparation of polyesters according to techniques well known in the art.

The use of thallium in combination with palladium can be viewed as an improvement over the use of bismuth in combination with palladium. One advantage is that the thallium containing catalyst can be effectively used more times than a comparable bismuth containing catalyst. Another advantage is that use of thallium results in consistently higher yields.

EXAMPLE 1

The following laboratory work was accomplished to illustrate practice of the invention.

A first run illustrating practice of the invention was accomplished wherein resorcinol bis(hydroxyethyl)ether (100 g; 0.51 mol) was dissolved in one liter of water containing NaOH (44 g; 1.1 mol.). The solution was warmed to 60° and a catalyst composed of 5% Pd and 2% Tl on carbon (10 g) was added. The resulting slurry was transferred to a two liter stirred autoclave which can be operated at pressures from 25 to 350 psig and temperatures from 50° to 200° C. and is agitated by a magnetic stirrer equipped with a turbine. The autoclave was equipped with a dip tube which allowed the reaction mixture to be sampled periodically while the reaction was taking place. The mixture was stirred at 960 rpms while air was passed through the mixture at a rate of 4 scfh with a head pressure of 50 psig. The autoclave was slowly heated to 80° C. at which point an exotherm occurred, and the autoclave was cooled at such a rate to maintain the temperature of the reaction mixture at 80° to 82° C. After two hours, the temperature of the mixture dropped and the consumption of oxygen ceased. The mixture was removed from the autoclave, the catalyst was filtered off, and the filtrate was acidified with 150 mL of 20% sulfuric acid. After cooling to room temperature (about two hours), the product was collected by filtration, washed with cold water (200 mL), and dried in a vacuum oven at 80°. The yield was 104 g (91%) and the purity was >99%. The result of this and the following examples are shown in the table.

The procedure of the first run was followed in nine additional runs except the amounts of thallium and palladium and the temperature were varied. The results of all the runs are shown below.

| Experiment No. | % Tl | % Pd | Temp. | Time | NaOH. conc. | % Yield |
|---|---|---|---|---|---|---|
| 1 | 0.5 | 5.0 | 80 | 120 | 1.10 | 91 |
| 2 | 2.5 | 5.0 | 80 | 120 | 1.10 | 81 |
| 3 | 2.5 | 5.0 | 100 | 120 | 1.10 | 96 |
| 4 | 2.5 | 5.0 | 80 | 120 | 1.10 | 91 |
| 5 | 5.0 | 5.0 | 100 | 120 | 1.10 | 94 |
| 6 | 4.0 | 5.0 | 80 | 120 | 1.10 | 75 |
| 7 | 0.5 | 5.0 | 100 | 120 | 1.10 | 91 |
| 8 | 1.0 | 10.0 | 100 | 120 | 1.10 | 89 |
| 9 | 4.0 | 5.0 | 80 | 120 | 1.10 | 65 |
| 10 | 4.0 | 5.0 | 80 | 120 | 1.65 | 91 |

EXAMPLE 2

A series of runs was completed to illustrate the enhanced yields of 1,3-phenylenedioxydiacetic acid when the thallium and palladium catalyst of the invention is used as opposed to the bismuth and palladium catalyst of the prior art.

Ten runs were made wherein resorcinol bis(hydroxyethyl)ether was oxidized to 1,3-phenylenedioxydiacetic acid as described in the above laboratory work using 10 g of catalyst comprised of 5% palladium and 2% bismuth on carbon. The same catalyst was used for all ten runs except an additional 10 g of virgin carbon added after each run. Ten similar runs were made except thallium was substituted for bismuth. The results of these runs are shown below.

| Experiment No. | % Yield Using Bismuth/Palladium Catalyst | % Yield Using Thallium/Palladium Catalyst |
|---|---|---|
| 1 | 97.2 | 98.3 |
| 2 | 95.0 | 97.5 |
| 3 | 86.2 | 94.0 |
| 4 | 85.5 | 97.1 |
| 5 | 80.2 | 91.2 |
| 6 | 84.9 | 89.8 |
| 7 | 68.8 | 91.3 |
| 8 | 69.8 | 89.5 |
| 9 | 75.2 | 90.9 |
| 10 | 78.6 | 86.5 |

These data show that % yields using the thallium/palladium catalyst are unobviously higher than % yields using the bismuth/palladium catalyst. The unobviously higher yields are particularly striking as the number of cycles with the same catalyst increases.

The invention has been described in detail with particular reference to preferred embodiments thereof, but it will be understood that varations and modifications can be effected within the spirit and scope of the invention.

I claim:

1. In a process for preparation of an aryloxyacetic acid corresponding to the structure:

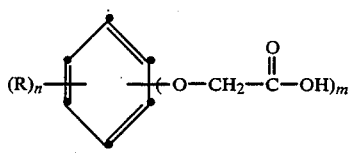

wherein
m represents 1 or 2, n represents the numeral which results from the difference between 6 and m and R either individually or independently of one another represents hydrogen, alkyl, cycloalkyl, aryl, aralkyl, alkoxy, cycloalkoxy, aryloxy, halogen, alkylcarbonyl, arylcarbonyl, carboxyl or nitro, or represents a benzene ring fused to the phenyl ring, comprising
   (a) preparing an aryloxyacetate corresponding to the structure:

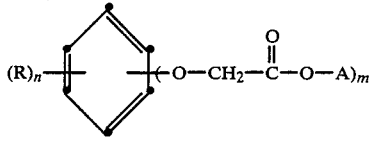

wherein n, m and R are as described above and A is an alkali metal cation by contacting an aryloxyethanol corresponding to the structure:

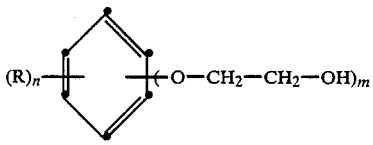

wherein m, n and R are as described above, with oxygen in an aqueous alkaline reaction medium at a temperature in the range of 0° C. to the boiling point of the reaction medium in the presence of a catalytic amount of a catalyst,
   (b) separating the aryloxyacetate from the catalyst, and
   (c) preparing the aryloxyacetic acid by contacting the separated acryloxyacetate with a mineral acid,
the improvement wherein the catalyst is comprised of palladium, thallium and carbon.

2. The process of claim 1 wherein R is hydrogen or a benzene ring fused to the phenyl ring.

3. The process of claim 1 wherein the pH is greater than 10.

4. The process of claim 1 wherein the temperature range is from about 80° to about 110° C.

5. The process of claim 1 wherein the mole ratio of thallium to palladium is 0.01 to 2.0:1.

6. The process of claim 1 wherein the mole ratio of thallium to palladium is 0.05 to 0.8:1.

7. In a process for preparation of an aryloxyacetic acid corresponding to the structure:

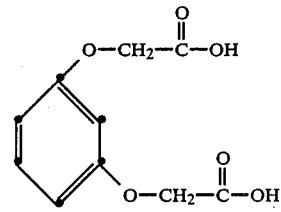

comprising
   (a) preparing an aryloxyacetate corresponding to the structure:

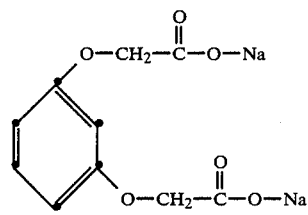

by contacting an aryloxyethanol corresponding to the structure:

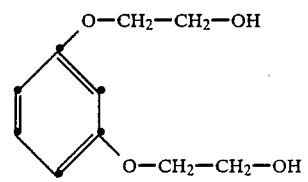

with oxygen in an aqueous alkaline reaction medium having a pH of greater than 10 at a temperature in the range of 80° to 90° C. in the presence of 5 to 10 weight percent, based on the weight of the aryloxyethanol, of a catalyst,
   (b) separating by filtration the aryloxyacetate from the catalyst, and
   (c) preparing the aryloxyacetic acid by contacting the separated aryloxyacetate with a mineral acid,
the improvement wherein the catalyst is comprised of palladium, thallium and carbon and the mole ratio of thallium to palladium is about 0.1 to 0.5:1.

* * * * *